United States Patent [19]

Hayashi

[11] Patent Number: 5,508,446
[45] Date of Patent: Apr. 16, 1996

[54] METHOD FOR PRODUCING ALKYL 3-PHTHALIDYLIDENEACETATE

[75] Inventor: Taketo Hayashi, Yao, Japan

[73] Assignee: Sumika Fine Chemicals Co., Ltd., Osaka, Japan

[21] Appl. No.: 316,486

[22] Filed: Oct. 3, 1994

[30] Foreign Application Priority Data

Oct. 6, 1993 [JP] Japan .................. 5-276077

[51] Int. Cl.⁶ ........................... C07D 307/78
[52] U.S. Cl. ............................... 549/305
[58] Field of Search ....................... 549/305

[56] References Cited

U.S. PATENT DOCUMENTS

| | | | |
|---|---|---|---|
| 2,483,371 | 9/1949 | Mowry | 549/305 |
| 4,182,622 | 1/1980 | Houbion et al. | 549/305 |
| 4,927,945 | 5/1990 | Briggs et al. | 549/305 |

FOREIGN PATENT DOCUMENTS 64-3173  1/1989  Japan.

OTHER PUBLICATIONS

"A Synthesis of Enol–Lactones" to Ingham et al, Aust. J. Chem., 1975, 28, 2499–510.

"Reformatsky Reaction: Carboxymethylenation of Cyclic Anhydrides and Reactions of Products Thereof" to Mylari et al, J. Org. Chem., 1991, 56, 2587–2589.

Chemical Abstracts, 111, 134180c (corresponding to JP–A–No. 64–3173) (1989).

Chemical Abstracts, 47, 12296 (1953).

"Reaction of Phthalic Anhydride with Ethyl Cyanoacetate: a Route to the 2H–Indeno [2,1–c]pyridine–1,9–dione, 2H–Indeno [2,1–c]pyridine–3,9–dione, 2H–Indeno[2,1–c]pyridazine–3,9–dione , and Indeno[2,1–c]pyran–1,9–dione Systems" to Renfrew et al, J. C. S. Perkin I, 1977, 84–90.

H. G. O. Becker et al, "Organikum; Organisch–chemisches Grundpraktikum, 16. bearbetiete Auflage" 1986, pp. 458–462.

Primary Examiner—Joseph E. Evans
Attorney, Agent, or Firm—Birch, Stewart, Kolasch & Birch

[57] ABSTRACT

A method for producing an alkyl 3-phthalidylideneacetate has the step of treating phthalic anhydride with a monoalkyl malonate or a salt thereof having the following formula:

$$MOCO-CH_2-COOR,$$

wherein M represents a hydrogen atom, K, Na, Li, or $NH_4$, and R represents a lower alkyl group having 1 to 5 carbon atoms. By using the above method, the desired alkyl 3-phthalidylideneacetate can be obtained at a high yield.

10 Claims, No Drawings

METHOD FOR PRODUCING ALKYL 3-PHTHALIDYLIDENEACETATE

BACKGROUND OF THE INVENTION

1. Field of the Invention

The present invention relates to a method for producing an alkyl 3-phthalidylideneacetate used as a synthesis intermediate for synthesizing 4-oxo-3-phthalazin-1-yl acetic acid useful as aldose reductase inhibitors for treatments of various chronic complications caused by diabetes, such as cataract, retinopathy, and neuropathy due to diabetes.

2. Discussion of the Related Art

Conventionally, the methods for producing an alkyl 3-phthalidylideneacetate are as follows:

(1) A method comprising the steps of treating phthalic anhydride with potassium acetate in acetic anhydride, treating with thionyl chloride, and then esterifying the product with an alcohol (see U.S. Pat. No. 2,483, 371);

(2) A method of treating phthalic anhydride with ethoxycarbonylmethylenetriphenylphosphorane in chloroform (see *Aust. J. Chem.*, 1975, 28, 2499–2510);

(3) A method comprising the steps of treating phthalic anhydride with a zinc-copper couple and ethyl bromoacetate (Reformatsky reaction), and dehydrating the reaction product with a concentrated sulfuric acid (*J. Org. Chem.*, 1991, 56, 2587–2589, and Japanese Pat. Laid-Open No. 64-3173); and (4) A method of treating phthalic anhydride with diethyl malonate in toluene (see J.C.S Perkin I, 1977, 84–90).

However, the method (1) comprises many steps, and the yield of the product is low. Also, it uses thionyl chloride, thereby making it industrially disadvantageous. In the method (2), triphenylphosphorane is used, and a mixture of cis-trans isomers is produced. In the method (3), the yield of the Reformatsky reaction is undesirably low, and metal waste water problems are incurred by the use of Zn and Cu. Further, the reaction is carried out in a two-step process. The method (4) is a two-step process, and the yield is extremely low (13%), making it industrially disadvantageous. The reasons for a low yield in the method (4) are not clear from the reference, but they may be presumably as follows:

Although the yield of the intermediate product of the two-step reaction in the method (4) is not disclosed in the reference, an extremely low yield (9%) of ethyl cyano(phthalidylidene)acetate, obtained by a similar reaction to the first step of the method (4), suggests a low yield of the intermediate in the method (4). In addition, a selective hydrolysis of only one of esters of diethyl malonate to give only a Z-isomer further lowers the product yield. Moreover, an E-isomer may be undesirably produced as a side product in the second step of the method (4).

Accordingly, a development of a more industrially advantageous method for producing an alkyl 3-phthalidylideneacetate is in demand.

SUMMARY OF THE INVENTION

An object of the present invention is to provide a novel method for industrially advantageously producing an alkyl 3-phthalidylideneacetate with high purity from an inexpensive starting material in a single step at a high yield.

In view of achieving the above object, various methods for producing alkyl 3-phthalidylideneacetates have been investigated. As a result, the present inventors have found that by using a monoalkyl malonate or a salt thereof in place of a dialkyl malonate used in the method (4), in which the product yield is the lowest among the several methods mentioned above, a desired alkyl 3-phthalidylideneacetate is produced in a one-step process from an inexpensive starting material at a high yield without using reagents with troublesome post-treatment and free from metal waste water problems. The present invention is based on these findings.

Specifically, the present invention is concerned with a method for producing an alkyl 3-phthalidylideneacetate, comprising the step of treating phthalic anhydride with a monoalkyl malonate or a salt thereof having the following formula:

wherein M represents a hydrogen atom, K, Na, Li, or $NH_4$, and R represents a lower alkyl group having 1 to 5 carbon atoms.

According to the method of the present invention, an alkyl 3-phthalidylideneacetate with high purity can be produced in a one-step process at a high yield from inexpensive starting materials such as phthalic anhydride and a monoalkyl malonate or a salt thereof. A monoalkyl malonate used as a main starting material in the method of the present invention has an extremely high reactivity, so that the method gives 3-phthalidylideneacetate at an excellent yield of 80% based on the main starting material under its optimum conditions. Since the method of the present invention has a different reaction mechanism from the method (4) mentioned above, a Z-isomer can be selectively produced. Furthermore, since conventionally required metal waste water treatment would not be necessary, the method of the present invention is remarkably industrially advantageous.

DETAILED DESCRIPTION OF THE INVENTION

The present invention will be detailed below.

A reaction scheme in the present invention is shown below.

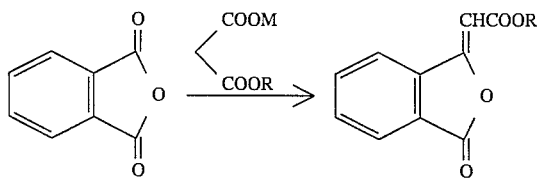

Phthalic anhydride used in the method of the present invention may be one as is industrially available at a low cost.

A selection of a malonic acid ester suitable for the reaction with phthalic anhydride is an important factor in the present invention. The malonic acid ester which can be used in the present invention is a monoalkyl malonate or a salt thereof having a general formula of $MOCO-CH_2-COOR$. Here, M represents a hydrogen atom, K, Na, Li, or $NH_4$. R represents a lower alkyl group having 1 to 5 carbon atoms, including methyl group, ethyl group, n-propyl group, isopropyl group, n-butyl group, isobutyl group, sec-butyl group, tert-butyl group, n-pentyl group, isopentyl group, and neopentyl group.

Preferred examples of the malonic acid esters suitably used in the present invention include monoethyl malonate, potassium ethyl malonate, monomethyl malonate, and potassium methyl malonate, all of which are industrially available. Alternatively, the malonic acid ester can be easily produced from diethyl malonate according to a conventional method (for instance, C.A., 47, 12296).

The amounts of phthalic anhydride and the malonic acid ester in the present invention are usually equimolar. However, in a case where an alkali metal salt of the malonic acid ester, such as potassium ethyl malonate and sodium ethyl malonate, is used, the amount of phthalic anhydride is preferably 1.5-folds to 2.5-folds, by mol, more advantageously about 2-folds, by mol, the amount of the alkali metal salt in order to neutralize metal hydroxide formed as a by-product. Other neutralizers, such as acetic acid, can be used for this purpose.

In the reaction in the present invention, a catalyst is added for accelerating the reaction. Examples of the catalysts include pyridine, triethylamine, piperidine, ammonium acetate, and mixtures thereof, with a preference given to pyridine.

When the alkali metal salts or the ammonium salts of an alkyl malonate, such as potassium ethyl malonate and ammonium ethyl malonate, are used, since the salts themselves function as catalysts, the reaction proceeds smoothly without adding any other catalysts.

The molar ratio of the amount of catalyst used to the amount of phthalic anhydride and malonic acid ester used is normally from 0.01/1 to 1/1. However, when the catalyst also functions as a reaction solvent, it may be normally from 1/1 to 20/1.

The reaction in the present invention is usually carried out in an inert solvent, including aromatic hydrocarbons, such as toluene and benzene, and ethers, such as diethylether and methylisopropylether. However, when pyridine, etc. are used as a catalyst, other solvents do not have to be added since they also function as a solvent.

The reaction temperature in the present invention is not particularly limited as long as the progress of the reaction is not mal-affected. The reaction temperature is normally from room temperature to 120° C., preferably from 50° to 120° C. from the viewpoint of increasing a reaction rate. The upper limit of the reaction temperature is normally a boiling point of the reaction solvent when the reaction is carried out under reflux.

The reaction time of the reaction in the present invention, which may vary depending upon the reaction temperature, is normally from 1 to 10 hours, and the reaction is terminated at a point where phthalic anhydride used as a starting material disappears.

After completion of the reaction, the desired alkyl 3-phthalidylideneacetate is isolated from the reaction mixture by a conventional method. For instance, in the case where an organic solvent such as toluene, etc. is used, separation is carried out by the steps of adding water to a reaction mixture at completion of the reaction; shaking the mixture and allowing it to stand to form two layers; separating out an organic layer; distilling off toluene from the organic layer; and recrystallizing the product from a solvent such as ethanol, etc.

In the case where the desired product is hardly dissolved in an organic layer, the separation is carried out by the steps of adding water to a reaction mixture at completion of the reaction; adding ammonium bicarbonate to the above mixture to neutralize phthalic acid formed as a by-product; filtering off precipitated crystals; and recrystallizing the product.

In the case where a pyridine solvent is used, the separation is carried out by the steps of adding an aqueous acetic acid solution to the reaction mixture to dissolve pyridine; cooling the obtained mixture; filtering off precipitated crystals; and recrystallizing the product.

EXAMPLES

The present invention will be described in further detail by means of the following working examples and reference example, without intending to limit the scope of the present invention thereto.

EXAMPLE 1

118.5 g (0.8 mol) of phthalic anhydride and 68.1 g (0.4 mol) of potassium ethyl malonate are added to 125 ml of pyridine. The mixture is heated at 90° to 100° C. for 2 hours. Here, the amount of phthalic anhydride is two-fold, by mol, the amount of potassium ethyl malonate in order to neutralize KOH formed as a by-product.

After carbon dioxide gas is no longer generated, the reaction mixture is cooled to room temperature, and 600 ml of 10%-aqueous acetic acid solution is added thereto. Thereafter, the reaction mixture is cooled to 10° C., and precipitated crystals are filtered off. After washing the crystals with 100 ml of water, they are dried under a reduced pressure, to give 54.0 g (0.247 mol) of ethyl (Z)-3-phthalidylideneacetate (melting point: 132° to 134° C.). The yield is 61.7%.

The physical properties are as follows:
EI-MS, 218 (M+), 190, 173, 146.
NMR (60 MHz, CDCl$_3$), δ (ppm): 1.3 (3H, t), 4.3 (2H, q), 5.9 (1H, s), 7.7–8.1 (4H, m).

EXAMPLE 2

59.2 g (0.4 mol) of phthalic anhydride, 26.4 g (0.2 mol) of monoethyl malonate, and 15.8 g (0.2 mol) of pyridine are added to 200 ml of toluene, and the reaction mixture is heated under reflux for 4 hours. After terminating the reaction, 100 ml of water is added to the reaction mixture, and an organic layer is separated out. The organic layer is washed with 100 ml of 5%-aqueous acetic acid solution, and toluene is distilled off under a reduced pressure. The residue thus obtained is recrystallized from ethanol, to give 32.7 g (0.15 mol) of ethyl (Z)-3-phthalidylideneacetate. The yield is 75.0%.

EXAMPLE 3

118.5 g (0.8 mol) of phthalic anhydride and 68.1 g (0.4 mol) of potassium ethyl malonate are added to 250 ml of toluene. The mixture is heated at 90° to 100° C. for 7 hours. After carbon dioxide gas is no longer generated, the reaction mixture is cooled to room temperature, and 500 ml of water is added thereto.

Next, 31.6 g (0.4 mol) of ammonium bicarbonate is added to neutralize the mixture solution. Crystals are filtered off. After washing the crystals with 100 ml of water, the washed crystals are further washed with 50 ml of ethanol. The washed crystals are dried under a reduced pressure, to give 69.8 g (0.32 mol) of ethyl (Z)-3-phthalidylideneacetate. The yield is 80.0%.

EXAMPLE 4

14.8 g (0.1 mol) of phthalic anhydride and 9.9 g (0.05 mol) of potassium tert-butyl malonate are added to 200 ml of toluene, and the reaction mixture is heated under reflux for 6 hours. After terminating the reaction, 100 ml of water is added, and an organic layer is separated out. The organic layer is washed with 100 ml of 5%-aqueous ammonium bicarbonate solution, and toluene is distilled off under a reduced pressure. The residue thus obtained is purified by column chromatography, to give 6.4 g (0.026 mol) of tert-butyl (Z)-3-phthalidylideneacetate. The yield is 52.0%.

EXAMPLE 5

The same procedures as in Example 3 are carried out except that sodium ethyl malonate is used in place of potassium ethyl malonate, to give 56.5 g (0.259 mol) of ethyl (Z)-3-phthalidylideneacetate. The yield is 64.8%.

EXAMPLE 6

The same procedures as in Example 3 are carried out except that ammonium ethyl malonate is used in place of potassium ethyl malonate, to give 45.8 g (0.21 mol) of ethyl (Z)-3-phthalidylideneacetate. The yield is 52.5%.

Reference Example 21.8 g (0.1 mol) of ethyl (Z)-3-phthalidylideneacetate obtained in Example 1 is added to 150 ml of ethanol. 6.3 g (0.1 mol) of 80%-hydrazine hydrate is added dropwise to the above mixture, and the reaction mixture is heated under reflux for 5 hours. After terminating the reaction, the reaction mixture is cooled to room temperature, and crystals are filtered off. The crystals are dried under a reduced pressure, to give 20.9 g (0.09 mol) of ethyl 4-oxo-3H-phthalazin-1-yl acetate (melting point: 181° C.). The yield is 90.0%.

The physical properties are as follows:
EI-MS, 232 (M+), 159, 130, 102.
NMR (60 MHz, DMSO-d$_6$), δ (PPM): 1.2 (3H, t), 4.0 (2H, s), 4.1 (2H, q), 7.7–8.3 (4H, m), 12.9 (1H, s).

The present invention being thus described, it will be obvious that the same may be varied in many ways. Such variations are not to be regarded as a departure from the spirit and scope of the invention, and all such modifications as would be obvious to one skilled in the art are intended to be included within the scope of the following claims.

What is claimed is:

1. A method for producing an alkyl 3-phthalidylideneacetate, comprising the step of treating phthalic anhydride with a monoalkyl malonate or a salt thereof having the following formula:

wherein M represents a hydrogen atom, K, Na, Li, or NH$_4$, and R represents a lower alkyl group having 1 to 5 carbon atoms.

2. The method according to claim 1, wherein said monoalkyl malonate or the salts thereof is selected from the group consisting of monoethyl malonate, potassium ethyl malonate, monomethyl malonate, and potassium methyl malonate.

3. The method according to claim 1, wherein the treating step is carried out in the presence of a catalyst selected from the group consisting of pyridine, triethylamine, piperidine, ammonium acetate, and mixtures thereof.

4. The method according to claim 3, wherein the amount of the catalyst to the amount of phthalic anhydride and the monoalkyl malonate or the salt thereof is 0.01/1 to 1/1 by molar ratio.

5. The method for producing an alkyl 3-phthalidylideneacetate according to claim 1, wherein R is selected from the group consisting of methyl, ethyl, n-propyl, isopropyl, n-butyl, isobutyl, sec-butyl, tert-butyl, n-pentyl, isopentyl and neopentyl.

6. The method for producing an alkyl 3-phthalidylideneacetate according to claim 1, wherein the amount of phthalic anhydride reacted with the monoalkyl malenate is an equimolar ratio.

7. The method for producing an alkyl 3-phthalidylideneacetate according to claim 1, wherein the amount of phthalic anhydride reacted with the salt of the monoalkyl malonate is 1.5 to 2.5 by mole the amount of the salt.

8. The method according to claim 3, wherein the treating step is carried out in the presence of an inert solvent.

9. The method according to claim 1, wherein the reaction temperature ranges from room temperature to 120° C.

10. The method according to claim 1, wherein the reaction temperature ranges from 50° to 120° C.

* * * * *